(12) United States Patent
Nicoletti et al.

(10) Patent No.: US 9,718,583 B2
(45) Date of Patent: Aug. 1, 2017

(54) COMPONENTS PACKAGING STRUCTURE FOR PHARMACEUTICAL CONTAINERS

(71) Applicants: STEVANATO GROUP INTERNATIONAL A.S., Bratislava (SK); FEDEGARI AUTOCLAVI S.P.A., Albuzzano (PV) (IT)

(72) Inventors: Fabiano Nicoletti, Mira (IT); Giuseppe Fedegari, Albuzzano (IT)

(73) Assignees: STEVANATO GROUP INTERNATIONAL A.S., Bratislava (SK); FEDEGARI AUTOCLAVI S.P.A., Albuzzano (PV) (IT)

( * ) Notice: Subject to any disclaimer, the term of this patent is extended or adjusted under 35 U.S.C. 154(b) by 0 days.

(21) Appl. No.: 14/423,119

(22) PCT Filed: Aug. 28, 2013

(86) PCT No.: PCT/IT2013/000230
§ 371 (c)(1),
(2) Date: Feb. 21, 2015

(87) PCT Pub. No.: WO2014/033766
PCT Pub. Date: Mar. 6, 2014

(65) Prior Publication Data
US 2015/0238263 A1    Aug. 27, 2015

(30) Foreign Application Priority Data
Aug. 30, 2012 (IT) ............... VI2012A0215

(51) Int. Cl.
*A61B 19/02*     (2006.01)
*A61M 5/00*      (2006.01)
(Continued)

(52) U.S. Cl.
CPC ............ *B65D 25/108* (2013.01); *A61B 50/33* (2016.02); *A61J 1/16* (2013.01); *A61M 5/002* (2013.01);
(Continued)

(58) Field of Classification Search
CPC ........ A61B 19/0271; A61B 2019/0277; A61B 50/33; A61B 2050/3007; A61J 1/16;
(Continued)

(56) References Cited

U.S. PATENT DOCUMENTS 2,523,877 A * 9/1950 Pestolesi ............ 206/366
2,655,283 A   10/1953 Moldt
(Continued)

FOREIGN PATENT DOCUMENTS

WO   2009/015862 A1   2/2009
WO   2011/135085 A1   11/2011

OTHER PUBLICATIONS

International Search Report dated Feb. 17, 2014.
Written Opinion of the International Searching Authority dated Feb. 17, 2014.

*Primary Examiner* — Stanton L Krycinski
(74) *Attorney, Agent, or Firm* — Hedman & Costigan, P.C.; James V. Costigan; Kathleen A. Costigan

(57) ABSTRACT

A components (17) packaging structure for pharmaceutical containers, comprising at least one tray (10), which has at least one open side for introducing and extracting at least one supporting shelf (11) which is parallel to a bottom plane (14) of the tray (10) and which rests in correspondence of the inner walls (15) of the tray (10); said supporting shelf (11) has a spatially predetermined distribution of first seats or cavities (13) within which closing components and/or generic accessories of said containers, such as rubber caps (17), nuts (20) with crimping snap or other types of sealing nuts and/or caps, are placed, so that the vertical axis of each
(Continued)

closure component is perpendicular to said bottom plane (14) of the tray (10), said structure thus constituting a guarantee of sterility and cleanliness of said closing components and/or generic accessories which are inserted in said seats or cavities (13).

6 Claims, 4 Drawing Sheets

(51) Int. Cl.
*B65D 25/10* (2006.01)
*B65D 39/00* (2006.01)
*B65D 65/02* (2006.01)
*A61J 1/16* (2006.01)
*A61B 50/33* (2016.01)
*B65B 7/28* (2006.01)
*A61J 7/00* (2006.01)
*A61J 1/14* (2006.01)
*A61B 50/30* (2016.01)

(52) U.S. Cl.
CPC ......... *B65D 39/0023* (2013.01); *B65D 65/02* (2013.01); *A61B 2050/3007* (2016.02); *A61J 1/1425* (2015.05); *A61J 7/0069* (2013.01); *B65B 7/2807* (2013.01)

(58) Field of Classification Search
CPC ... A61J 1/1425; A61J 7/0069; B01L 3/50853; A61M 5/002; B65D 25/108; B65D 39/0023; B65D 65/02
USPC ............................. 211/85.13, 85.18; 206/366
See application file for complete search history.

(56) References Cited

U.S. PATENT DOCUMENTS

| | | | | |
|---|---|---|---|---|
| 3,491,894 | A * | 1/1970 | Brown | 211/74 |
| 4,130,978 | A * | 12/1978 | Cohen | 53/444 |
| 4,349,109 | A * | 9/1982 | Scordato et al. | 206/562 |
| 4,599,314 | A * | 7/1986 | Shami | 435/305.3 |
| 5,004,103 | A * | 4/1991 | Connors et al. | 206/372 |
| 5,112,574 | A * | 5/1992 | Horton | 422/569 |
| 5,366,088 | A * | 11/1994 | Hill et al. | 206/499 |
| 5,392,914 | A * | 2/1995 | Lemieux et al. | 206/499 |
| 5,441,702 | A * | 8/1995 | Lemieux et al. | 422/526 |
| 5,827,745 | A * | 10/1998 | Astle | 436/54 |
| 5,893,618 | A * | 4/1999 | LePage et al. | 312/265.6 |
| 6,007,779 | A * | 12/1999 | Lemieux et al. | 422/526 |
| 6,164,044 | A * | 12/2000 | Porfano et al. | 53/471 |
| 6,286,678 | B1 * | 9/2001 | Petrek | 206/443 |
| 6,328,933 | B1 * | 12/2001 | Labriola et al. | 422/564 |
| 6,534,015 | B1 * | 3/2003 | Viot et al. | 422/564 |
| 7,060,226 | B2 * | 6/2006 | Jessop et al. | 422/526 |
| 7,191,904 | B2 * | 3/2007 | Wescott, III | 211/74 |
| 7,232,038 | B2 * | 6/2007 | Whitney | 211/74 |
| 7,258,240 | B2 * | 8/2007 | Wescott, III | 211/74 |
| 7,296,678 | B2 * | 11/2007 | Raynal-Olive et al. | 206/439 |
| 7,428,807 | B2 * | 9/2008 | Vander Bush et al. | 53/425 |
| 7,431,157 | B2 * | 10/2008 | Porret et al. | 206/439 |
| 7,963,396 | B2 * | 6/2011 | Vanderbush et al. | 206/524.8 |
| 8,100,263 | B2 * | 1/2012 | Vanderbush et al. | 206/524.8 |
| 8,118,167 | B2 * | 2/2012 | Togashi et al. | 206/534.1 |
| 8,206,665 | B2 * | 6/2012 | Tsutsumi et al. | 422/552 |
| 8,360,238 | B2 * | 1/2013 | Nicoletti | 206/560 |
| 8,460,622 | B2 * | 6/2013 | Motadel | 422/564 |
| 8,485,357 | B2 * | 7/2013 | Song et al. | 206/366 |
| D699,859 | S * | 2/2014 | Motadel | D24/227 |
| 2002/0069616 | A1 | 6/2002 | Odell | |
| 2006/0054523 | A1 | 3/2006 | Porret | |
| 2008/0173563 | A1* | 7/2008 | Perot | 206/438 |
| 2009/0026107 | A1* | 1/2009 | Ross | 206/570 |
| 2009/0226345 | A1* | 9/2009 | Tsutsumi et al. | 422/99 |
| 2013/0048531 | A1* | 2/2013 | Nicoletti | 206/557 |

* cited by examiner

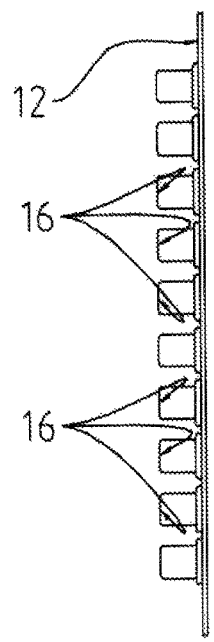
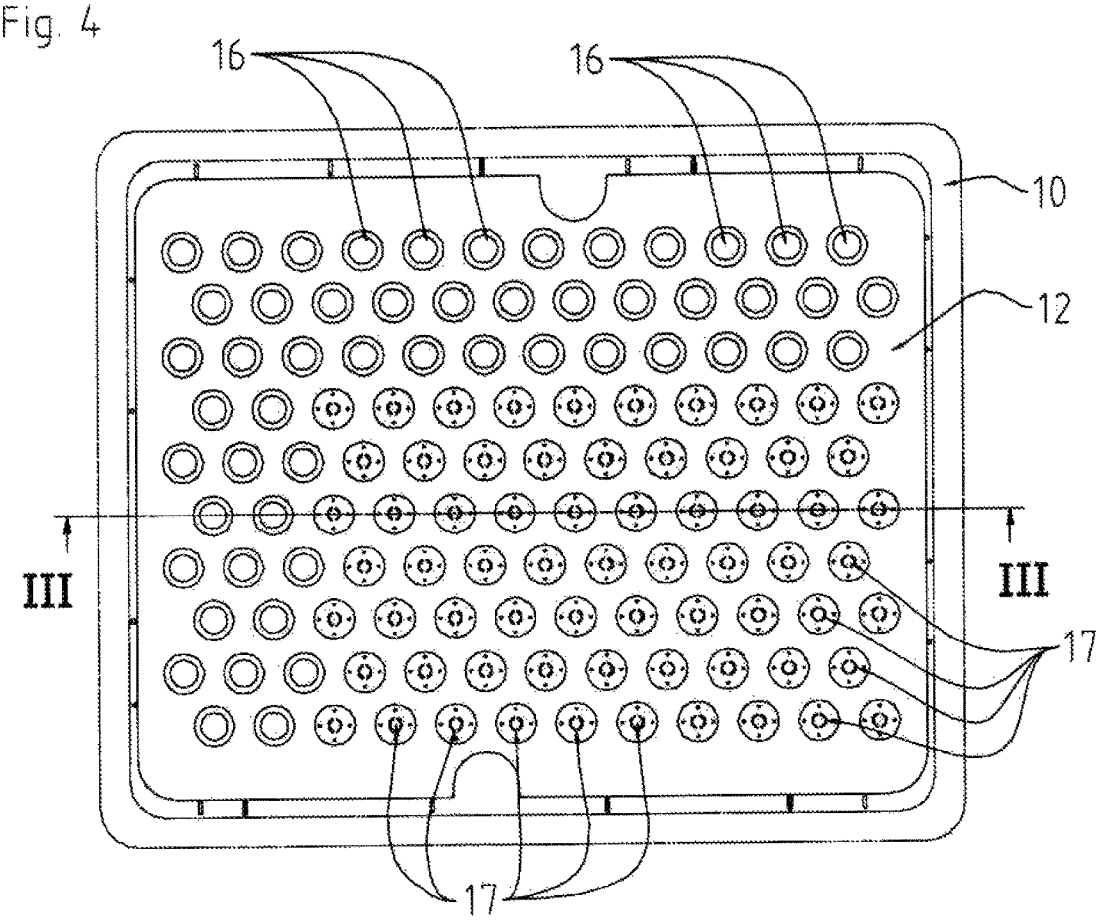

COMPONENTS PACKAGING STRUCTURE FOR PHARMACEUTICAL CONTAINERS

The present invention generally relates to a components packaging structure for pharmaceutical containers.

In particular, the invention relates to a components packaging structure, wherein the components have technical features such that they must be kept in a controlled and isolated environment, as well as a clean, sterile, non-toxic and physically or chemically stable environment, until their use or their application in the implementation process (filling and closing) of ampoules, vial, syringes and other pharmaceutical containers.

The known components packaging structures for pharmaceutical containers comprise a tray made of plastic material and having a closed bottom which carries an internal plane or matrix (the so-called "nest") made of plastic material and having a series of housing holes where the containers are placed in a vertical position as described in WO2009/015862A1.

Some containers, such as syringes, are kept in their positions thanks to the fact that a perimeter flange of the container leans against the edge of the housing holes, while other containers which do not have protruding parts require specific elements for being housed within the holes.

The plastic tray is sealed by a porous membrane filter, such as a paper filter or a Tyvek® filter, and is also protected by a further closed container consisting of a flexible film that has an opening concealed by a porous filtering or Tyvek® membrane.

Therefore, the packaging structure comprises at least two overlapping sterility barriers which are able to stop any microbiological or particles contamination; it is also possible to add other containers in order to have more sterility barriers.

Said isolated packages are then placed within containers made of plastic or corrugated cardboard, which have the size and weight suitable to be manually handled during the packing and unpacking operations.

The containers are generally stacked and placed on pallets before being subjected to a final sterilization cycle (with gas).

Finally, when the products have to be used, they are sent into a controlled contamination area, for example a sterile zone, by means of an aseptic filling process; the operation consists in unpacking the units, in opening the outer container with reduced contamination (the operation is normally carried out under a laminar ultra-clean air flow, thus protecting the surface), in extracting the packaging after a biological decontamination of the external surface and in placing said packaging into the aseptic zone, before removing the Tyvek® filter of the tray.

However, the known components packaging structure for pharmaceutical containers, as described, have a limited use flexibility, since they cannot be used universally and effectively for packaging other components which are provided for assembling the pharmaceutical containers, such as rubber stoppers for closing the vials, sealing rings made for example of aluminum and/or snap-locking devices which are placed in correspondence with the container opening.

Moreover, even the above mentioned components must necessarily be kept in a controlled and isolated sterile environment until their use and therefore they are still packaged inside respective and ready-to-use sterile packages too.

The different components are thus oriented in the right direction for example by means of a vibrant bolus and then sorted on a number of tracks where an automated device picks them up and guide them to an assembly final position.

It is clear that the above described system does not allow the automated management of the different components sets through the containers' handling, assembling and eventually closing automated devices, because, for example, if two components are to be mounted on a single container (such as a rubber cap and a sealing ring) the system must be duplicated, with the consequent additional operating costs and the relative difficulties for changing the containers' sizes by means of the automated components' picking, handling and assembling devices.

Moreover, each package able to specifically contain the relative component must be prepared, cleaned and sterilized each time the containers' sizes are changed. An object of the present invention is therefore to overcome the above mentioned drawbacks of the prior art and particularly to provide a components packaging structure for filling pharmaceutical containers which is multipurpose and which enables, at the same time, after the containers filling by means of automatic machines and without the aid of any operator, an automated management of the different sets of other accessories which can be used from time to time.

Another object of the present invention is to provide a components packaging structure for pharmaceutical containers, which ensures the sterilization of the closing and locking components and of the accessories that are typically required to complete the containers' filling process, which ensures the maintenance of their qualitative characteristics, their integrity, their identification and traceability, as well as the safe transfer and assembly of said accessories.

A further object of the invention is to provide a components packaging structure for pharmaceutical containers, which makes easy the components' and containers' handling and assembling operations, thereby reducing the total cost of the final product.

Advantageously, the packaging structure according to the invention allows to have the different components or accessories (such as plugs, clamps, snap-locks, etc.) to be placed on the pharmaceutical container, so that they are immediately ready to use, since they are oriented in a correct direction and positioned in a right place and they can thus picked up and assembled by means of automated picking and mounting devices (robots), which can be pre-programmed depending on the size of the different containers; the robot can be also programmed to perform the correct sequences of the handling and assembling steps for finalizing the pharmaceutical container.

This allows the use of dedicated production lines for small quantities and for different sizes, thereby achieving significant savings in operating costs, simplicity and efficiency of the handling and assembling operations, as well as speed and efficiency in changing the containers' sizes.

Further characteristics and advantages of the components packaging structure for pharmaceutical containers, which is the object of the present invention, will become clear from the following description relating to a preferred embodiment and from the alleged drawings in which:

FIG. 2 is a side view of the element of FIG. 1, according to the present invention;

FIG. 4 is a top plan view of said first embodiment of the components packaging structure for pharmaceutical containers of FIG. 3, according to the present invention;

Figure 1:
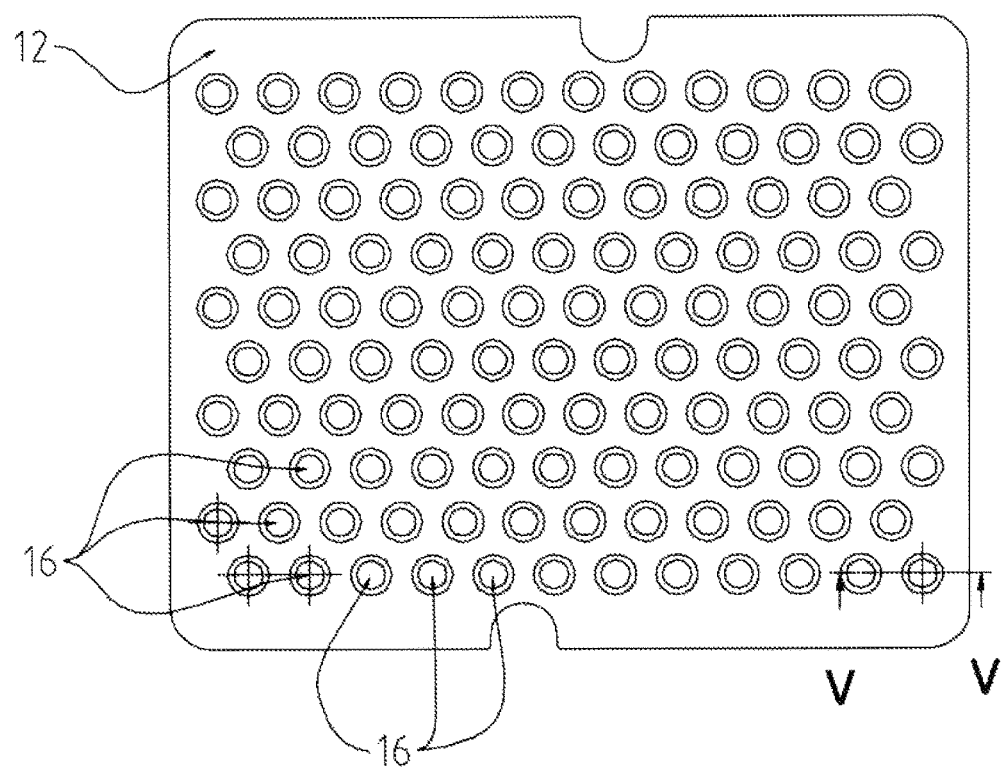
FIG. 1 is a top plan view of an element used in a first embodiment of the components packaging structure for pharmaceutical containers, according to the present invention.
Figure 3:
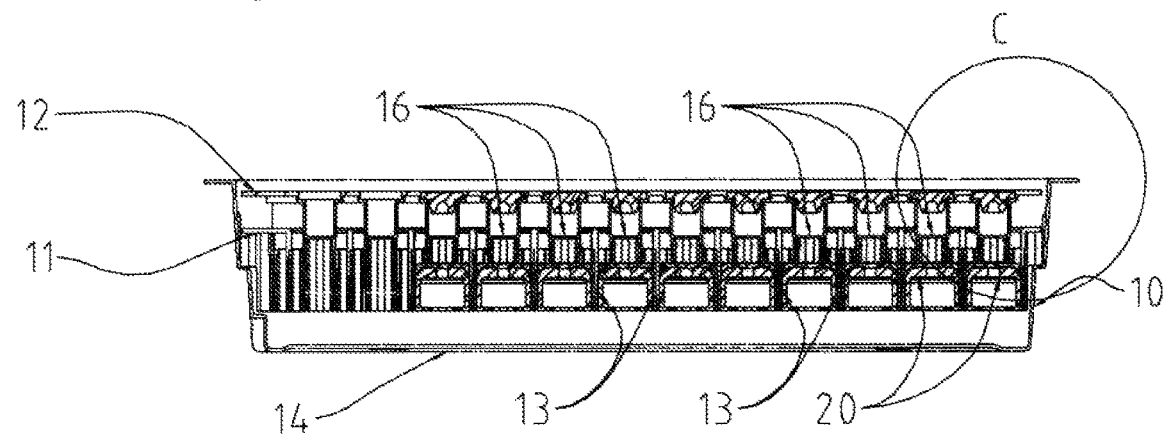
FIG. 3 is a sectional view along the line III-III of FIG. 4 of said first embodiment of the components packaging structure for pharmaceutical containers, according to the present invention.
Figure 5:
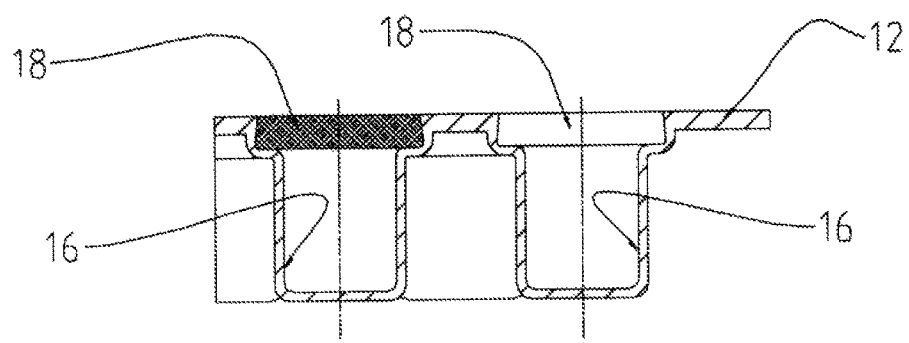
FIG. 5 is a sectional view taken along the line V-V of FIG. 1, according to the invention.
Figure 6:
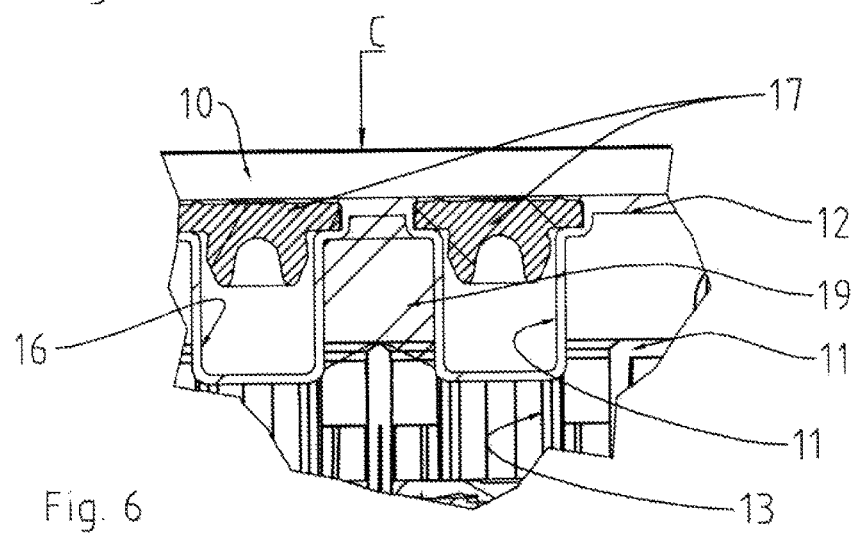
FIG. 6 shows an enlargement of the detail indicated with C in FIG. 3.

With reference to the above mentioned drawings, the components packaging structure for pharmaceutical containers which is the object of the present invention comprises a tray 10, which is normally made of plastic material and which has an open upper side for inserting and extracting a first flat element or shelf 11 supporting the pharmaceutical containers; said first flat element 11 is also made of plastic material, such as polypropylene, and is positioned parallel to the bottom plane 14 of the tray 10.

Said open upper side of the tray 10 is sealed with a filtering porous membrane and the tray 10 may also have a protective wrapping or cover for its transfer in a controlled area (for example, an area where takes place the containers' filling); the protective cover can be open or closed and can include a rapid transfer door.

Moreover, each protective cover may contain one or more stacked trays 10 and/or one or more supporting flat elements 11 and is formed at least partially by a sheet made of a material which is selectively permeable to a traditional sterilization process.

Figure 7:
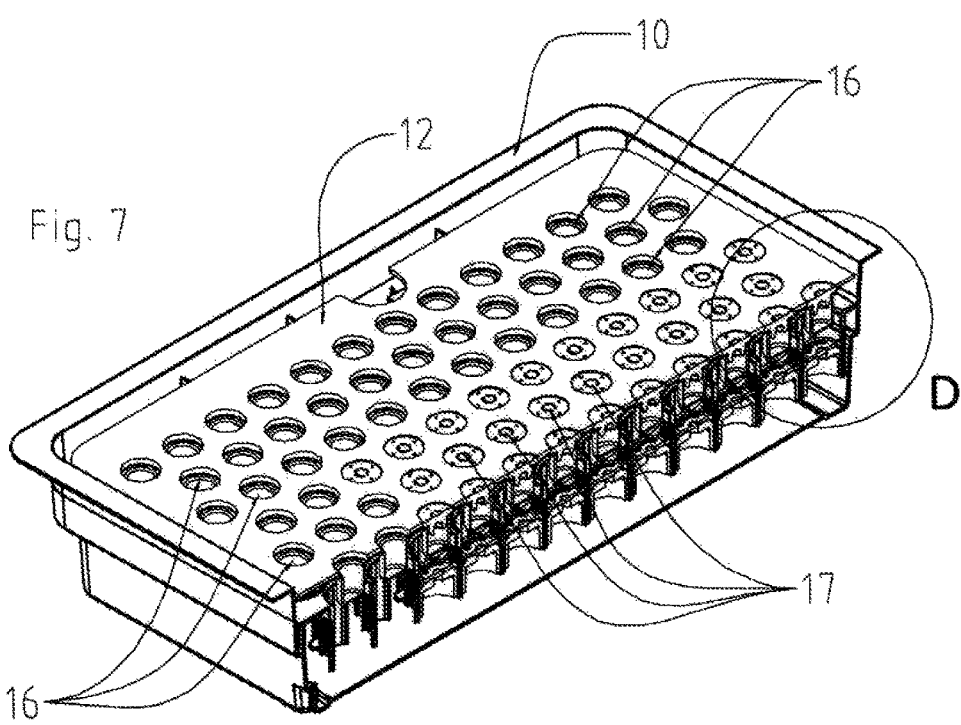
FIG. 7 is a cross-section perspective view of the components packaging structure for pharmaceutical containers of the previous figures, according to the present invention.
Figure 8:
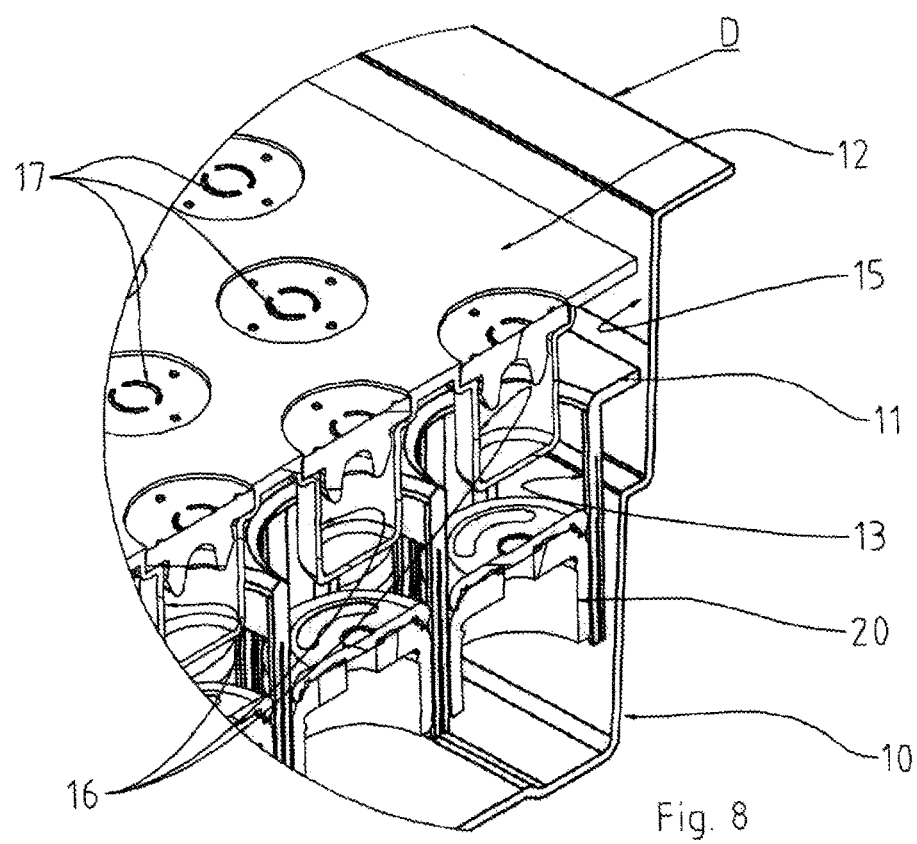
FIG. 8 shows an enlargement of the detail indicated with D in FIG. 7.
Figure 9:
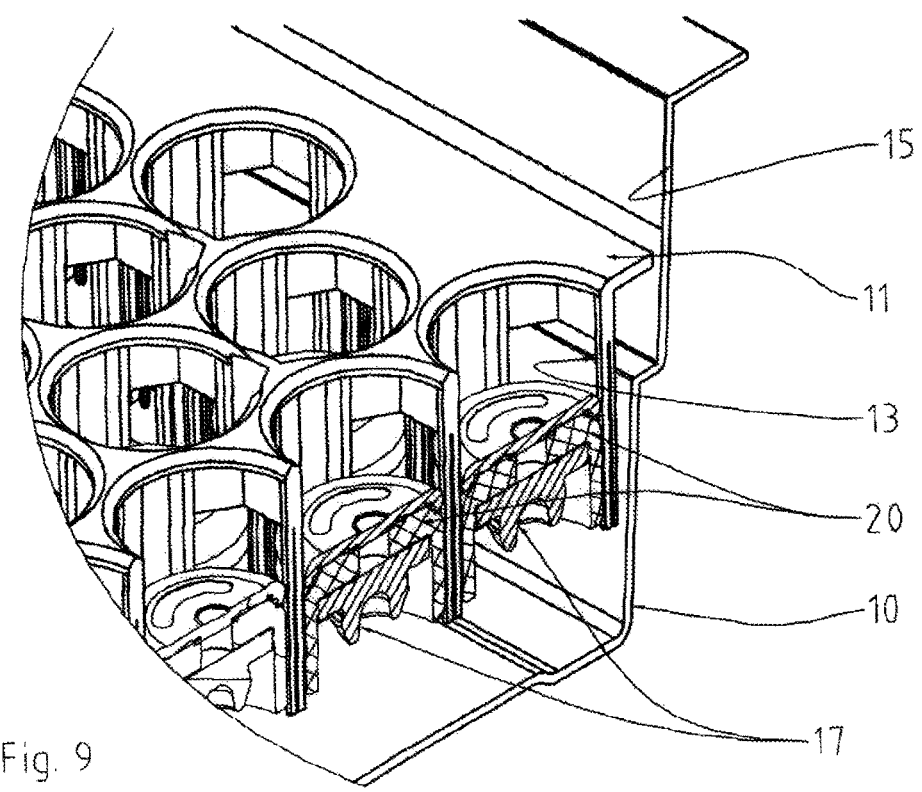
FIG. 9 shows an enlargement of a detail of a possible alternative embodiment of the components packaging structure for pharmaceutical containers, according to the present invention.

The supporting flat element 11 has a flat upper surface and a substantially rectangular shape and has pairs of parallel opposing edges resting on a side shoulder formed on the inner walls 15 of the tray 10 (as shown in detail in the alleged FIGS. 7 and 8); said edges are stable in position through abutment means, such as for example projections made on the tray 10 which counteract with respective cavities having a conjugated shape and made on the flat element 11 (or, conversely, projections made on the flat element 11 which counteract with respective cavities provided on the tray 10).

Furthermore, said supporting flat element 11 has a predetermined spatial distribution of vertical seats 13, within which containers' closures, such as sealing rings 20 made for example of aluminum, and/or snap-locking devices are placed at a predetermined distance one from another; said closures and/or locking devices have their longitudinal axis perpendicular to the bottom plane 14 of the tray 10.

According to a first embodiment of the present invention, a further supporting flat element or shelf 12 is superimposed to the supporting flat element 11; the flat element 12 has also a flat surface and is also shaped so as to have a series of cavities or seats 16 having an upper surface 18 of a suitable geometry and placed in correspondence of respective vertical seats 13 of the flat element 11.

In particular, the components which are provided for completely assembling the pharmaceutical containers, such as the rubber plugs 17, are inserted and held in position within the cavity 16 of the supporting flat element 12, while the aluminum and/or plastic seals, such as the ferrules 20 and/or the containers' snap-locking devices (bottles, cartridges) are also placed within the seats 13 of the lower flat element 11.

Specifically, the cavities 16 of the supporting flat element 12 are made so that the rubber plugs 17 are housed and maintained in a right position and in a correct orientation; the rubber plugs 17 may be placed one for each cavity 16 at the upper surface 18 corresponding to the input area of the pharmaceutical components.

The upper flat surface of the supporting flat element 12 also allows to place the protective membrane above the cavities 16, thus allowing to insert each single supporting flat element 11, 12 or a series of stacked supporting flat elements 11, 12 inside a further protective cover.

Alternatively, the components such as the rubber plugs 17 and the crimping ferrules 20 can also be pre-assembled together before being placed in the seats 16; for example, the rubber plugs 17 and the locking devices of said plugs 17 can be firstly assembled together and then positioned, as one piece, within the respective cavities 16 of the supporting flat element 12, while, whether the locking devices have a diameter which is substantially equal to or lower than the diameter of the glass container, it is possible to use the supporting flat element 11 to also house the locking devices (such as the rubber plugs 17 and the ferrules or nuts 20), which are pre-assembled inside the cavities 13 of the supporting flat element 11.

Furthermore, both supporting flat elements 11, 12 have the same external overall dimensions and the same arrangement of the cavities or seats 13, 16, so as to be easily stacked, and said cavities or seats 13, 16 are also advantageously shaped according to a matrix, in order to protect the closure components, such as the plugs 17 and/or the ferrules 20, from shocks, contacts, deformation, surface pressures, etc.

According to other embodiments, more than two supporting flat elements 11, 12 can be stacked.

Respective shaped areas 19 are also provided among the cavities 16 of the supporting flat element 12; the areas 19 have a shape suitable for ensuring a right integrity and strength of the structure and a perfect vertically centering between the supporting flat elements 11 and 12, and between the seats 13 and 16 of the respective flat elements 11 and 12.

According to a further embodiment of the present invention, it is also possible to avoid the supporting flat element 12 and thus provide for inserting the supporting flat element 11, the locking devices, such as the rubber plugs or stoppers 17, and the crimping ferrules 20, which are already pre-assembled and directly coupled together, inside the seats 13 of the supporting flat element 11; advantageously, this solution allows to avoid the use of a component (the supporting flat element 12), thus savings production and operative costs, since the relative sterilization problems which are related to the handling of said supporting flat element 12 are also avoided.

The packaging structure thus formed is used for directly and automatically feeding the pharmaceutical containers and the related closure components, such as the caps 17 and the ferrules 20, which are contained therein and which are placed in prefixed spatially positions, to a process machine for their manipulation. Typically, the process machine comprises a device or automated arm (robot) including a gripping member suitable for handling each closure component.

The supporting flat elements 11, 12, filled with the respective locking or closure components, which are grouped in oriented rows, after being extracted from the tray 10 (without the upper closing element), are moved toward a picking position of the robot head, which shall, after having filled the pharmaceutical containers, assembly the different closure or locking components, such as the rubber plugs 17, the crimping ferrules 20 or other snap-locking devices and/or seals able to close the pharmaceutical container.

It is therefore clear that, according to the present invention, it is possible to simultaneously treat, along only one filling aseptic line, independent supporting flat elements 11, 12 which contain the locking or closure components, such as the rubber plugs or stoppers 17, the snap-locking devices, seals and/or crimping ferrules 20, related to the size of the pharmaceutical containers, thus directly obtaining, in a short time and in an extremely effective way, the finished product.

The aseptic filling line requires, in fact, that the containers and the locking or closure components are preliminarily prepared (washed and sterilized) and are subsequently introduced into said aseptic area without any components' or environment's contamination.

Therefore, along said containers' and closure components' transfer line, physical (e-beam, plasma, etc.) and/or chemical (vaporized hydrogen peroxide, peracetic acid, dioxide chlorine, etc.) processes, which are able to obtain a surface decontamination, are carried out.

In another embodiment of the invention, the trays 10, closed with the filtering membrane, are packaged within a container having a sterile transfer door, which can be placed in correspondence of the wall of the aseptic zone, where the corresponding fixed portion of the sterile transfer door is provided; so, the trays 10 are directly transferred into the aseptic zone without any contamination.

In any case, according to the present invention, said transfer line can be planned so as to transfer both the supporting flat elements housing the pharmaceutical containers and the supporting flat elements 11, 12 containing the respective closure components, in order to obtain a complete sterility and cleanliness of all the elements through a single process and to perform in a quick and effective way a change of the size of the glass containers and of the related closure components. If more than two supporting flat elements 11, 12 housing the closure components are provided, they can be stacked together in a single outer container, in order to further reduce operating costs and improve the treatment effectiveness.

The technical features of the components packaging structure for pharmaceutical containers, which is the object of the present invention, are clear from the above description, as well as the related advantages are also clear.

It is finally clear that other variations may be made to the packaging structure of the invention, without departing from the principles of novelty inherent in the inventive idea as claimed in the alleged claims, as it is clear that in the practical implementation of the invention, the materials, shapes and sizes of the technical details can be any, depending on requirements, and can be replaced with other technically equivalent.

The invention claimed is:

1. Components packaging structure for pharmaceutical containers for pharmaceutical components, comprising at least one tray (10), which has at least one open side for introducing and extracting at least one first supporting flat shelf (11) which is parallel to a bottom plane (14) of the at least one tray (10), said packaging structure having inner walls (15), wherein said at least one first supporting flat shelf (11) is positioned lower than a second supporting shelf (12) and rests in correspondence of the inner walls (15) of said at least one tray (10) and has a spatially predetermined distribution of first seats or cavities (13) within which each of said first seats or cavities has closing components of said containers selected from rubber caps or plugs (17), and ferrules or nuts (20) with a crimping snap, so that a vertical axis of each closing component is perpendicular to said bottom plane (14) of the at least one tray (10), said structure thus constituting a sterile and clean environment, said at least one first supporting flat shelf (11) of said closing components selected from rubber caps or plugs (17), and ferrules or nuts (20) with a crimping snap is coupled with said second supporting shelf (12), which is parallel to said at least one first supporting flat shelf (11) of said closing components, and said second supporting shelf (12) has a prefixed spatially distribution of second seats or cavities (16) provided in correspondence of said first seats or cavities (13) of said at least one first supporting flat shelf (11) of said closing components, characterized in that additional closing components selected from said rubber caps or plugs (17) are inserted and held in position within said second seats or cavities (16) of said second supporting shelf (12) while aluminum or plastics seals or said ferrules or nuts (20) or snap-locking devices are placed within said first seats or cavities (13) of said at least one first supporting flat shelf (11).

2. Components packaging structure according to claim 1, characterized in that said rubber caps or plugs (17) are placed in said second seats or cavities (16) and at an upper surface (18) of said second seats or cavities (16).

3. Components packaging structure according to claim 1, characterized in that said open side of the at least one tray (10) is sealed by means of at least one filtering porous membrane.

4. Components packaging structure according to claim 1, characterized in that said at least one tray (10) is enclosed within at least one protective enclosure, which is formed, at least partially, from a sheet made of a selectively permeable material.

5. Components packaging structure according to claim 4, characterized in that said protective enclosure contains said at least one tray (10) and/or stacked said trays (10) and/or one or more of said at least one first supporting flat shelf (11) and second supporting shelf (12) of said containers and/or of said closing components.

6. Components packaging structure according to claim 1, characterized in that between said second seats or cavities (16) of said second supporting shelf (12) respective shaped areas (19) are centered in the vertical direction between said at least one first supporting flat shelf (11) and said second supporting shelf (12) and between said first and second seats or cavities (13, 16) of the respective at least one first supporting flat shelf (11) and second supporting shelf (12).

\* \* \* \* \*